United States Patent [19]
Gaffney et al.

[11] Patent Number: 5,210,336
[45] Date of Patent: May 11, 1993

[54] OXIDATION OF OLEFIN TO GLYCOL

[75] Inventors: Anne M. Gaffney; John A. Sofranko, both of West Chester, Pa.

[73] Assignee: ARCO Chemical Technology, L.P., Wilmington, Del.

[21] Appl. No.: 825,473

[22] Filed: Jan. 24, 1992

Related U.S. Application Data

[63] Continuation-in-part of Ser. No. 312,265, Feb. 21, 1989, abandoned.

[51] Int. Cl.[5] ...................... C07C 29/12; C07C 29/03; C07C 29/48; C07C 31/20
[52] U.S. Cl. .................................... 568/860; 549/229; 549/230; 568/821; 568/833; 568/858
[58] Field of Search ................ 568/860, 858, 821, 833

[56] References Cited

U.S. PATENT DOCUMENTS

| 2,780,654 | 2/1957 | Robertson et al. | 568/860 |
| 4,483,996 | 11/1984 | Jacobson | 549/524 |
| 4,824,969 | 4/1989 | Austin et al. | 568/860 |

FOREIGN PATENT DOCUMENTS

| 2050376 | 1/1981 | United Kingdom | 568/860 |

Primary Examiner—Joseph E. Evans
Attorney, Agent, or Firm—William C. Long

[57] ABSTRACT

A process is provided for the conversion of an olefin to the corresponding glycol wherein a mixture of olefin, oxygen, carbon dioxide and water is reacted in a solvent at supercritical conditions with respect to the reaction mixture.

7 Claims, No Drawings

OXIDATION OF OLEFIN TO GLYCOL

BACKGROUND OF THE INVENTION

Related Applications

This application is a continuation-in-part of copending application Ser. No. 07/312,265 filed Feb. 21, 1989 and now abandoned.

FIELD OF THE INVENTION

The present invention relates to the oxidation of olefins such as propylene to the corresponding glycol wherein the oxidation is carried out in a solvent such as carbon dioxide at conditions which are supercritical with respect to the reaction mixture.

DESCRIPTION OF THE PRIOR ART

The catalytic oxidation of olefins to the corresponding glycols is a known reaction which is generally carried out in aqueous acidic media at conditions which are not supercritical. See for example German patents 1948786 and 1948838 as well as U.K. published application 2050376.

Problems associated with such systems include the necessity for corrosion-resistant materials of construction and difficulties in production separation.

The reaction conditions taught in Mee, et al 1. U.K. 2,050,376 are not supercritical with respect to the reaction mixture. The highest temperatures and pressure suggested by Mee, et al. at page 1, lines 39-44 are a temperature of 225° C. and pressure of 150 bars. Actually, this latter figure is suspect since the broad range of pressure is taught to be 1-100 bars and the preferred range 1-150 bars. Even assuming a pressure of 150 bars, a temperature of 225° C. and the maximum 5 mols $CO_2$ per liter of aqueous reaction mixture (page 1, lines 36-38), the reaction of Mee, et al. is not at supercritical conditions. In fact, as calculated by the Peng Robinson Equation of State, at these extreme values the reaction mixture of Mee, et al. is not in the supercritical regime but rather comprises 87% liquid phase and 13% vapor phase as contrasted with the single phase required for supercriticality.

Olefin oxidation at supercritical conditions using carbon dioxide solvent and thallic oxide catalyst to produce the corresponding olefin oxide is known. See U.S. Pat. No. 4,483,996.

Likewise, the oxidation of olefins to alkylene carbonates using a catalytic system consisting of iodine or iodide and an oxygen transfer material such as manganese dioxide is known. See U.S. Pat. No. 4,009,183. In this latter patent, water is employed as solvent alone or in admixture with miscible polar solvent such as acetonitrile; a broad pressure range is disclosed, but the examples use only 35 atm or less. Reaction temperatures are well below the critical temperatures of water and acetonitrile.

BRIEF DESCRIPTION OF THE INVENTION

In accordance with the present invention, olefins are oxidized to the corresponding glycol by reaction of olefin, oxygen, carbon dioxide and water in a solvent such as carbon dioxide at conditions which are supercritical with respect to the reaction mixture. A catalyst system, preferably a heterogeneous solid system, is employed.

DETAILED DESCRIPTION OF THE INVENTION

The present invention is applicable generally to the conversion of olefins to the corresponding glycol. Preferably unsubstituted linear or cyclic olefins having 2 to 12 carbon atoms are converted. Examples include ethylene, propylene, the butenes, cyclohexene, 1-decene, 1-dodecene, cyclododecene, and the like. Propylene is the preferred olefin.

Molecular oxygen is provided as the oxidant. Air may be used as may pure oxygen or oxygen diluted with various inert gases.

Water is a necessary reagent and is provided in amount at least stoichiometrically equivalent to olefin which is converted, i.e., a mol of water per mol of olefin converted.

Carbon dioxide is also a necessary reagent. Where carbon dioxide solvent is employed, the solvent provides the necessary carbon dioxide for the olefin conversion. Where a different solvent is employed, carbon dioxide reactant must be added.

While not intending to be bound by theory, it is believed that the olefin conversion first proceeds to the carbonate and, at the conditions employed, the carbonate reacts with water to form the product glycol. While carbon dioxide is essential, there is no net consumption of this material.

Elevated temperatures above the critical temperature of the reaction mixture are necessary to carry out the reaction. Temperatures broadly ranging from about 70° C. to 400° C., preferably 100° C. to 250° C. are employed.

A solvent is employed which forms the primary component of the reaction mixture. Reaction conditions are employed which are supercritical with respect to the reaction mixture at which the reaction mixture, with the exception of solid catalyst materials, forms a homogeneous single phase fluid. The preferred solvent is carbon dioxide. Materials which are reagents such as water or olefin can also function effectively as solvent. Mixtures of materials may be employed as the solvent. Conditions in the reaction zone must be maintained supercritical with respect to the reaction mixture in accordance with the invention. Preferably pressures which are supercritical with respect to the reaction mixture and which are in excess of 75 atmospheres are employed, especially pressures of 100 to 500 atmospheres.

Catalyst systems comprised of copper and iodine components together with an oxygen transfer agent are employed. A preferred catalyst system comprises CuI and $Cu_2O$ with $MnO_2$ as oxygen transfer agent to facilitate reoxidation of cuprous components. For ease of product separation, the catalyst system is suitably supported on a solid such as MgO. An illustrative system is represented by CuI (5 wt. % as Cu), $Cu_2O$ (10 wt. % as Cu) and Na $MnO_4$ (12.5 wt. %) on MgO.

As a particular feature of invention, it has been found that greatly improved results are achieved where the catalyst system is supported on a high surface area support such as gamma-alumina. Other supports include silica, silica-alumina and the like. By high surface area is meant surface area in excess of 20 $m^2/g$, preferably 50 to 250 $m^2/g$.

The catalyst components can be supported by conventional impregnation and calcination procedures, the catalyst system comprising 2 to 50 wt/ %. preferably 10 to 40 wt. % of the final composition of catalyst plus support.

The following examples illustrate the invention.

EXAMPLE 1

A feed mixture comprises of 6.29 moles $CO_2$, 0.574 moles $O_2$, 0.487 moles propylene, 0.380 moles nitrogen, and 1.11 moles water was charged to a pressure reactor to which also was added 5.51 grams of a heterogeneous catalyst system comprising $CaI_2$, (5 wt. % as Ca), CuI (5 wt. % as Cu, $Cu_2O$ (10 wt. % as Cu) on $MnO_2$ support.

The catalyst was contained in a basket which was rotated during the reaction. The reaction was carried out for 10 hours at 146° C. and 2217 psig.

About 3.8% of the $O_2$ was converted, selectivity to propylene glycol was 91.5%.

EXAMPLE 2

Practice of the invention was carried out in a continuous flow, fixed bed reactor. Reaction conditions were supercritical with respect to the reaction mixture and were 140° C. and 2000 psig; residence time was 1 minute. The feed mixture comprised by volume 7% propylene, 2% oxygen, 10% nitrogen, 15% water and 66% carbon dioxide.

In one run, Run 1, the catalyst system of Example 1 was employed whereas in Run 2 the catalyst system was supported on high surface area (156 m²/g) gamma-alumina. Specifically, for Run 2 the gamma-alumina was impregnated with calcium iodide, copper iodide, manganese acetate and copper nitrate and calcined in air at 200° C. to produce a supported catalyst containing $CaI_2$ (5 wt. % as Ca), CuI (5 wt% as Cu), $Cu_2O$ (10 wt. % as Cu) and $MnO_2$ (10 wt. % as Mn). In each case the wt. % is based on the total of catalyst plus support. Table 2 shows the results obtained.

TABLE 2

|  | Run 1 | Run 2 |
| --- | --- | --- |
| Propylene Conversion, % | 2.9 | 50.0 |
| Productivity, $\frac{\text{grams PG*}}{\text{gram catalyst/hr}}$ | 0.13 | 2.0 |
| Selectivity, % | | |
| to PG* | 100 | 95 |
| to PC** | 0 | 5 |

*propylene glycol
**propylene carbonate

From the above, it can be seen that propylene conversion and propylene glycol productivity greatly increased through use of catalyst supported on high surface area support.

We claim:

1. The process for the catalytic conversion of an olefin to the corresponding glycol which comprises reacting the olefin, oxygen, carbon dioxide and water in the presence of a catalyst in a solvent at conditions which are supercritical with respect to the reaction mixture.

2. The process of claim 1 wherein said olefin is propylene.

3. The process of claim 1 wherein said solvent is carbon dioxide.

4. The process of claim 1 wherein the catalyst is a heterogeneous solid catalyst.

5. The process of claim 1 wherein the conditions which are supercritical with respect tot he reaction mixture are a temperature in the range of 70 to 400° C. and a pressure in excess of 75 atmospheres.

6. The process for the catalytic conversion of an olefin to the corresponding glycol which comprises reacting the olefin, oxygen, carbon dioxide and water in the presence of a heterogeneous solid catalyst comprises of a catalyst system supported on a high surface area solid support in a solvent at conditions which are supercritical with respect to the reaction mixture.

7. The process of claim 6 wherein the heterogeneous solid catalyst comprises a catalyst system supported on a high surface area gamma alumina.

* * * * *